US010731176B2

(12) United States Patent
Hey et al.

(10) Patent No.: US 10,731,176 B2
(45) Date of Patent: Aug. 4, 2020

(54) DIG-305 INSECTICIDAL CRY TOXINS

(71) Applicant: DOW AGROSCIENCES LLC, Indianapolis, IN (US)

(72) Inventors: Timothy D. Hey, Zionsville, IN (US); Meghan L. F. Frey, Indianapolis, IN (US); Xiaoping Xu, Carmel, IN (US); Audrey Jane Etter, Indianapolis, IN (US); Elizabeth Caldwell, Indianapolis, IN (US); Ted Letherer, Indianapolis, IN (US); Navin Elango, Indianapolis, IN (US); Kenneth Narva, Zionsville, IN (US)

(73) Assignee: DOW AGROSCIENCES LLC IN (US)

( * ) Notice: Subject to any disclaimer, the term of this patent is extended or adjusted under 35 U.S.C. 154(b) by 0 days.

(21) Appl. No.: 15/541,290

(22) PCT Filed: Dec. 16, 2015

(86) PCT No.: PCT/US2015/066189
§ 371 (c)(1),
(2) Date: Jun. 30, 2017

(87) PCT Pub. No.: WO2016/109214
PCT Pub. Date: Jul. 7, 2016

(65) Prior Publication Data

US 2017/0369538 A1 Dec. 28, 2017

Related U.S. Application Data

(60) Provisional application No. 62/097,852, filed on Dec. 30, 2014.

(51) Int. Cl.

| | |
|---|---|
| *C12N 15/82* | (2006.01) |
| *A01N 37/46* | (2006.01) |
| *A01N 63/10* | (2020.01) |
| *C07K 14/325* | (2006.01) |

(52) U.S. Cl.
CPC ......... *C12N 15/8286* (2013.01); *A01N 37/46* (2013.01); *A01N 63/10* (2020.01); *C07K 14/325* (2013.01); *Y02A 40/162* (2018.01)

(58) Field of Classification Search
None
See application file for complete search history.

(56) References Cited

U.S. PATENT DOCUMENTS

| | | | | |
|---|---|---|---|---|
| 5,527,883 | A * | 6/1996 | Thompson | A01N 63/00 530/350 |
| 5,827,514 | A | 10/1998 | Bradfisch et al. | |
| 2013/0247254 | A1 | 9/2013 | Lira et al. | |

FOREIGN PATENT DOCUMENTS

| | | | |
|---|---|---|---|
| JP | 2002 335967 A | | 11/2002 |
| WO | WO 2012/135501 | * | 10/2012 |

OTHER PUBLICATIONS

Saraswathy et al, 2004, Electronic Journal of Biotechnology 7:180-190.*

Balasubramanian, Periasamy; et al.: "Cloning and Characterization of the Crystal Protein-Encoding Gene of *Bacillus thuringiensis* subsp. *yunnanenis*", Applied and Environmental Microbiology, Jan. 2002 (Jan. 2002), vol. 68, No. 1, pp. 408-411.

Chambers, Judith A.; et al.: "Isolation and Characterization of a Novel Insecticidal Crystal Protein Gene from *Bacillus thuringeiensis* subsp. *aizawai*", Journal of Bacteriology, Jul. 1991 (Jul. 1991), vol. 173, No. 13, pp. 3966-3976.

Crickmore, N.; et al.: "Revision of the Nomenclature for the Bacillus thuringiensis Pesticidal Crystal Proteins", Microbiology and Molecular Biology Reviews, Sep. 1998 (Sep. 1998), vol. 62, No 3, pp. 807-813.

Donovan, William P.; et al.: "Characterization of Two Genes Encoding Bacillus thuringiensis Insecticidal Crystal Proteins Toxic to *Coleoptera* Species", Applied and Environmental Microbiology, Dec. 1992 (Dec. 1992), vol. 58, No. 12, pp. 3921-3927.

Takebe, S.; et al.: "Bacillus thuringiensis crystal protein gene", GenBank Accession BAB78602.

Vazquez-Padron, R. I.; et al.: "Cryptic endotoxic nature of Bacillus thuringiensis Cry1Ab insecticidal cyrstal protein", FEBS Letters, Jul. 16, 2004 (Jul. 16, 2004), vol. 570, pp. 30-36.

International Preliminary Report on Patentability, International Search Report, and Written Opinion for International Application PCT/US15/66189, dated Feb. 12, 2016.

Takebe, S.; et al.: "Bacillus thuringiensis crystal protein gene", GenBank Accession BAB78603.

Takebe, S.; et al.: "Bacillus thuringiensis crystal protein gene", GenBank Accession BAB78604.

* cited by examiner

*Primary Examiner* — Anne Kubelik

(57) ABSTRACT

DIG-305 insecticidal protein toxins, polynucleotides encoding such toxins, and transgenic plants that produce such toxins are disclosed. Also disclosed are methods for using such toxins to control insect pests in plants, especial crop plants. Methods for preparing transgenic plants expressing the protein toxins and methods for detecting the claimed toxins and polynucleotides in transgenic plants are disclosed.

18 Claims, No Drawings

Specification includes a Sequence Listing.

DIG-305 INSECTICIDAL CRY TOXINS

CROSS-REFERENCE TO RELATED APPLICATIONS

This application is a national stage entry under 35 USC § 371(b) of PCT International Application No. PCT/US2015/066189, filed Dec. 16, 2015, and claims the benefit of and priority to U.S. Provisional Application Ser. No. 62/097,852 filed Dec. 30, 2014. Each of these applications is expressly incorporated herein by reference.

FIELD OF THE DISCLOSURE

The present invention relates generally to the field of molecular biology as applied to agricultural sciences. Methods of making and using the claimed nucleic and amino acid sequences in the development of t incorporated protectants in transgenic plant cells and plants are disclosed herein.

BACKGROUND OF THE DISCLOSURE

*Bacillus thuringiensis* (B.t.) is a soil-borne bacterium that produces pesticidal crystal proteins known as delta endotoxins or Cry proteins. Cry proteins are oral intoxicants that function by acting on midgut cells of susceptible insects. Some Cry toxins have been shown to have activity against nematodes. An extensive list of delta endotoxins is maintained and regularly updated at the *Bacillus thuringiensis* Toxin Nomenclature web site maintained by Neil Crickmore. (See Crickmore et al. 1998, page 808).

Coleopterans are a significant group of agricultural pests that cause extensive damage to crops each year. Examples of coleopteran pests include corn rootworm, alfalfa weevil, boll weevil, and Japanese beetle. The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in North America: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; and *D. u. undecimpunctata* Mannerheim. The United States Department of Agriculture currently estimates that corn rootworms cause $1 billion in lost revenue each year, including $800 million in yield loss and $200 million in treatment costs. Cry toxins, including members of the Cry1B, Cry1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C (Frankenhuyzen, 2009) families have insecticidal activity against coleopteran insects.

Although production of the currently-deployed Cry proteins in transgenic plants can provide robust protection against the aforementioned pests, thereby protecting grain yield, adult pests have emerged in artificial infestation trials, indicating less than complete larval insect control. Additionally, development of resistant insect populations threatens the long-term durability of Cry proteins in insect pest control. Lepidopteran insects resistant to Cry proteins have developed in the field for *Plutella xylostella* (Tabashnik, 1994), *Trichoplusia ni* (Janmaat and Myers, 2003, 2005), and *Helicoverpa zea* (Tabashnik et al., 2008). Coleopteran insects likewise have developed resistance in the field to Cry proteins (Gassman et al. PLoS ONE July 2011|Volume 6|Issue 7|e22629). Insect resistance to B.t. Cry proteins can develop through several mechanisms (Heckel et al., 2007; Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease.

There is interest in the development of new Cry proteins that provide additional tools for management of coleopteran insect pests. Cry proteins with different modes of action produced in combination in transgenic plants would prevent the development of insect resistance and protect the long term utility of B.t. technology for insect pest control.

BRIEF SUMMARY OF THE DISCLOSURE

The present invention is based on the discovery of insecticidal toxins based on the Cry protein toxin designated herein as DIG-305, including variants of DIG-305, nucleic acids encoding these toxins, methods of controlling pests using the toxins, methods of producing the toxins in transgenic host cells, and transgenic plants that express the toxins. The predicted amino acid sequence of native DIG-305 toxin in SEQ ID NO:2 indicates that DIG-305 is best classified to the Cry32 family.

As described in Example 1, a nucleic acid encoding the DIG-305 protein was discovered and isolated from a B.t. strain internally designated by Dow AgroSciences LLC as PS246F10 also known as DBt11519. The nucleic acid sequence for the full length coding region was determined, and the full length protein sequence was deduced from the nucleic acid sequence. The nucleic acid sequence encoding DIG-305 toxin is given in SEQ ID NO:1. A BLAST search using the insecticidal protein sequence as a query found that DIG-305 toxin protein has 89% sequence identity to the closest insecticidal toxin Cry32Ca1 (BAB78602) and 91% sequence identity to the closest publically disclosed sequence (AGU13873, US20140096281). Thus, DIG-305 represents a new subclass within the Cry32 family of proteins.

The DIG-305 toxins can be used alone or in combination with other Cry toxins, such as Cry34Ab1/Cry35Ab1 (DAS-59122-7), Cry3Bb1 (MON88017), Cry3A (MIR604), chimeric Cry3A/Cry1Ab (eCry3.1Ab, FR8A, Event 5307, WO 2008/121633 A1), CryET33 and CryET34, Vip1A, Cry1Ia, CryET84, CryET80, CryET76, CryET71, CryET69, CryET75, CryET39, CryET79, TIC809, TIC810, and CryET74 to control the development of resistant Coleopteran insect populations. Further, DIG-305 toxins can be used alone or in combination with other Cry toxins that control the development of other pest populations, such as, for example, Cry1F, Cry1Ab, Vip Cry2A, Cry1Da, Cry Ha, and Cry1Ac to control the development of lepidopteran resistant insect populations.

DIG-305 insecticidal toxins may also be used in combination with RNAi methodologies for control of other insect pests. For example, DIG-305 insecticidal toxins can be used in transgenic plants in combination with a dsRNA for suppression of an essential gene in WCR or another insect pest (Baum et. al., 2007). Such target genes include, for example, vacuolar ATPase, ARF-1, Act42A, CHD3, EF-1α, ROP, RNAPII, and TFIIB in corn rootworm. An example of a suitable target gene is vacuolar ATPase, as disclosed in WO2007035650.

In one embodiment, the invention provides an isolated, treated, or formulated DIG-305 insecticidal toxin polypeptide comprising a core toxin segment selected from the group consisting of (a) the amino acid sequence of residues from approximately 2 to approximately 685 of SEQ ID NO:2; (b) an amino acid sequence having at least 90% sequence identity to the amino acid sequence of residues from approximately 2 to approximately 685 of SEQ ID NO:2; and (c) an amino acid sequence of residues from approximately 2 to approximately 685 of SEQ ID NO:2, with up to 20 amino acid substitutions, deletions, or modifications that do not adversely affect expression or activity of the toxin of SEQ ID NO:2; or an insecticidal active fragment of either (a), (b), or (c).

In certain embodiments the DIG-305 insecticidal toxin polypeptide comprises (a') the amino acid sequence of residues from approximately 2 to 685 of SEQ ID NO:2; (b') an amino acid sequence having at least 90% sequence identity to the amino acid sequence of residues from approximately 2 to 685 of SEQ ID NO:2; and (c') an amino acid sequence of residues from approximately 2 to 685 of SEQ ID NO:2, with up to 20 amino acid substitutions, deletions, or modifications that do not adversely affect expression or activity of the toxin of SEQ ID NO:2; or an insecticidal active fragment of either (a'), (b') or (c'). In further embodiments, the DIG-305 insecticidal toxin polypeptide of (a), (b), (c), (a'), (b') or (c') can be linked to a C-terminal protoxin, e.g., the C-terminal protoxin of cry1Ab or cry1Ac/cry1Ab chimeric toxin.

In another embodiment the invention provides an isolated, treated, or formulated DIG-305 insecticidal toxin polypeptide comprising a DIG-305 core toxin segment selected from the group consisting of a (a) polypeptide comprising the amino acid sequence of residues 1 to 1241 of SEQ ID NO:2; (b) polypeptide comprising an amino acid sequence having at least 90% sequence identity to the amino acid sequence of residues 1 to 1241 of SEQ ID NO:2; and (c) polypeptide comprising an amino acid sequence of residues 1 to 1241 of SEQ ID NO:2, with up to 20 amino acid substitutions, deletions, or modifications that do not adversely affect expression or activity of the toxin of SEQ ID NO:2; or an insecticidal active fragment of either (a), (b), or (c).

In another embodiment the invention provides a plant comprising a DIG-305 insecticidal toxin disclosed herein. In another embodiment the invention provides a method for controlling a pest population comprising contacting said population with a pesticidally effective amount of a DIG-305 insecticidal toxin disclosed herein. In another embodiment the invention provides an isolated nucleic acid that encodes a DIG-305 insecticidal toxin disclosed herein. In another embodiment the invention provides a DNA construct comprising a nucleotide sequence that encodes a DIG-305 insecticidal toxin operably linked to a heterologous promoter that is not derived from *Bacillus thuringiensis* and is capable of driving expression in a plant. The invention also provides a transgenic plant that comprises the DNA construct stably incorporated into its genome and a method for protecting a plant from a pest comprising introducing the construct into said plant.

By "isolated" applicants mean that the nucleotide or polypeptide molecules have been removed from their native environment and have been placed in a different environment by the hand of man. Thus, isolated nucleotide and polypeptide molecules include DNA or protein molecules that have been purified, concentrated, or otherwise rendered substantially free of *Bacillus thuringiensis* cellular material. Embodiments of isolated DIG-305 insecticidal polypeptide or nucleotide molecules can have less than about 30%, less than about 20%, less than about 10%, less than about 9%, less than about 8%, less than about 7%, less than about 6%, less than about 5%, less than about 4%, less than about 3% or less than about 2%, or less than about 1% (by dry weight) of contaminating protein (e.g., from *Bacillus thuringiensis*). When the isolated DIG-305 insecticidal polypeptide or nucleotide embodiments is recombinantly produced, then the culture medium material, chemical precursors, and/or or non-DIG-305 insecticidal polypeptide or nucleotide represent less than about 30%, less than about 20%, less than about 10%, less than about 5%, less than about 4%, less than about 3% or less than about 2%, or less than about 1% (by dry weight) of the isolated DIG-305 insecticidal polypeptide or nucleotide.

BRIEF DESCRIPTION OF THE SEQUENCES

SEQ ID NO:1 is a DNA sequence encoding a DIG-305 toxin; 3726 nt.

SEQ ID NO:2 is a deduced DIG-305 protein sequence; 1241 aa.

SEQ ID NO:3 is a maize-optimized DNA sequence encoding full length DIG-305; 3723 nt.

DETAILED DESCRIPTION OF THE DISCLOSURE

DIG-305 Insecticidal Toxins:

In addition to the full length DIG-305 toxin of SEQ ID NO:2, the invention encompasses insecticidal active variants thereof. By the term "variant", applicants intend to include fragments, certain deletion and insertion mutants, and certain fusion or chimeric proteins. DIG-305 includes three-domains generally associated with a Cry toxin. As a preface to describing variants of the DIG-305 toxin that are included in the invention, it will be useful to briefly review the architecture of three-domain Cry toxins in general and of the DIG-305 protein toxin in particular.

A majority of *Bacillus thuringiensis* delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., 1989). The protoxin segment may thus convey a partial insect specificity for the toxin by limiting the accessibility of the core to the insect by reducing the protease processing of the toxin molecule (Haider et al., 1986) or by reducing toxin solubility (Aronson et al., 1991). B.t toxins, even within a certain class, vary to some extent in length and in the precise location of the transition from the core toxin segment to protoxin segment. The transition from core toxin segment to protoxin segment will typically occur at between about 50% to about 60% of the full length toxin. SEQ ID NO:2 discloses the 1241 amino acid sequence of the partial DIG-305 polypeptide, of which the N-terminal 685 amino acids comprise a DIG-305 core toxin segment.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where helix five is surrounded by six amphipathic helices. This domain has been implicated in pore formation and shares homology with other pore forming proteins including hemolysins and colicins. Domain I of the DIG-305 protein comprises amino acid residues approximately 1-320 of SEQ ID NO:2.

Domain II is formed by three anti-parallel beta sheets packed together in a beta prism. The loops of this domain play important roles in binding insect midgut receptors. In Cry1A proteins, surface exposed loops at the apices of Domain II beta sheets are involved in binding to Lepidopteran cadherin receptors. Cry3Aa Domain II loops bind a membrane-associated metalloprotease of Leptinotarsa decemlineata Say (CPB) in a similar fashion (Ochoa-Campuzano et al., 2007). Domain II shares homology with certain carbohydrate-binding proteins including vitelline and jacaline. Domain II of the DIG-305 protein comprises amino acid residues approximately 320-525 of SEQ ID NO:2.

Domain III is a beta sandwich of two anti-parallel beta sheets. Structurally this domain is related to carbohydrate-binding domains of proteins such as glucanases, galactose oxidase, sialidase, and others.

Conserved B.t. sequence blocks 2 and 3 map near the N-terminus and C-terminus of Domain 2, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO1991001087, WO1995006730, U.S. Pat. Nos. 5,736,131, 6,204,246, 6,780,408, WO1998022595, U.S. Patent Application No. 20090143298, and U.S. Pat. No. 7,618,942). Domain III of the DIG-305 protein comprises amino acid residues approximately 526-685 of SEQ ID NO:2.

In lepidotperan insects it has been reported that Cry1A toxins bind certain classes of receptor proteins including cadherins, aminopeptidases and alkaline phosphatases, others remain to be identified (Honée et al., 1991; Pigott and Ellar, 2007). In coleopteran insects, two receptors have been identified for Cry3Aa; in Colorado potato beetle an ADAM metalloprotease (Biochemical and Biophysical Research Communications 362 (2007) 437-442), in Tenebrio a cadherin has been identified (THE JOURNAL OF BIOLOGICAL CHEMISTRY VOL. 284, NO. 27, pp. 18401-18410, Jul. 3, 2009). Given the diversity of Bacillus thuringiensis toxins and pests it is anticipated that additional receptors will be identified that will include additional classes of proteins and membrane surface substituents.

It has been reported that α-helix 1 of Domain I is removed following receptor binding. Aronson et al. (1999) demonstrated that Cry1Ac bound to brush border membrane vesicles (BBMV) was protected from proteinase K cleavage beginning at residue 59, just after α-helix 1; similar results were cited for Cry1Ab. Gomez et al. (2002) found that Cry1Ab oligomers formed upon BBMV receptor binding lacked the α-helix 1 portion of Domain I. Also, Soberon et al. (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al. (2007) described Cry1Ab fragments of 43 kDa and 46 kDa that retained activity on Mediterranean corn borer (Sesamia nonagrioides). These fragments were demonstrated to include amino acid residues 116 to 423 of Cry1Ab; however the precise amino acid sequences were not elucidated and the mechanism of activity of these proteolytic fragments is unknown. The results of Gomez et al. (2002), Soberon et al. (2007) and Diaz-Mendoza et al. (2007) contrast with those of Hofte et al. (1986), who reported that deletion of 36 amino acids from the N-terminus of Cry1Ab resulted in loss of insecticidal activity.

Amino Terminal Deletion Variants of DIG-305

In one of its aspects, the invention provides DIG-305 variants in which all or part of one or more α-helices are deleted to improve insecticidal activity and avoid development of resistance by insects. These modifications are made to provide DIG-305 variants with improved attributes, such as improved target pest spectrum, potency, and insect resistance management. In some embodiments of the subject invention, the subject modifications may affect the efficiency of protoxin activation and pore formation, leading to insect intoxication. More specifically, to provide DIG-305 variants with improved attributes, step-wise deletions are described that remove part of the DNA sequence encoding the N-terminus. Such deletions remove all of α-helix 1 and all or part of α-helix 2 in Domain I, while maintaining the structural integrity of the α-helices 3 through 7. The subject invention therefore relates in part to improvements to Cry protein efficacy made by engineering the α-helical components of Domain I for more efficient pore formation. More specifically, the subject invention provides improved DIG-305 proteins designed to have N-terminal deletions in regions with putative secondary structure homology to α-helices 1 and 2 in Domain I of Cry1 proteins.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshaysky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al. (1998) found that in plants the N-end rule includes basic and aromatic residues. It may be that proteolytic cleavage by plant proteases near the start of α-helix 3 of subject B.t. insecticidal proteins expose a destabilizing N-terminal amino acid. Such processing may target the cleaved proteins for rapid decay and limit the accumulation of the B.t. insecticidal proteins to levels insufficient for effective insect control. Accordingly, for certain examples of N-terminal deletion variants that begin with one of the destabilizing amino acids, a codon that specifies a G (glycine) amino acid can be added between the translational initiation methionine and the destabilizing amino acid.

Protease Sensitivity Variants

Insect gut proteases typically function in aiding the insect in obtaining needed amino acids from dietary protein. The best understood insect digestive proteases are serine proteases, which appear to be the most common type (Englemann and Geraerts, 1980), particularly in lepidopteran species. Coleopteran insects have guts that are more neutral to acidic than are lepidopteran guts. The majority of coleopteran larvae and adults, for example CPB, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in CPB. Gillikin et al. (1992) characterized the proteolytic activity in the guts of western corn rootworm larvae and found primarily cysteine proteases. U.S. Pat. No. 7,230,167 disclosed that a protease activity attributed to cathepsin G exists in western corn rootworm. The diversity and different activity levels of the insect gut proteases may influence an insect's sensitivity to a particular B.t. toxin.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to affect protein processing at desired deletion points within the midgut of susceptible larvae. Serine proteases that can be exploited in such fashion include lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on lepidopteran pests such as *Ostrinia nubilalis, Diatraea grandiosella, Helicoverpa zea, Agrotis Ipsilon, Spodoptera frugiperda, Spodoptera exigua, Diatraea saccharalis, Loxagrotis albicosta*, Coleopteran pests such as western corn rootworm, southern corn rootworm, northern corn rootworm (i.e. *Diabrotica* spp.), and other target pests.

Serine proteases of the same family such as trypsin, chymotrypsin and cathepsin G-like protease, coleopteran cysteine proteases such as cathepsins (B-like, L-like, O-like, and K-like proteases) (Koiwa et al., 2000; and Bown et al., 2004), Coleopteran metalloproteases such as ADAM10 (Ochoa-Campuzano et al., 2007), and coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites is within the "spacer" region between α-helix2B and α-helix3. A second preferred location for the introduction of protease cleavage sites is within the spacer region between α-helix3 and α-helix4. Modified DIG-305 insecticidal toxin proteins are generated either by gene deletion or by introduction of protease cleavage sites to provide improved activity on insect pests including but not limited corn rootworm, alfalfa weevil, boll weevil, Japanese beetle, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible (Bailey et al., 1992; U.S. Pat. No. 6,046,053). Thus, in some embodiments, B.t. Cry proteins which have been activated by means of proteolytic processing, for example, by proteases prepared from the gut of an insect, may be characterized and the N-terminal or C-terminal amino acids of the activated toxin fragment identified. DIG-305 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-305 Toxin

The separate domains of the DIG-305 toxin, (and variants that are 90%, 91%, 92%, 93, 94%, 95%, 96%, 97%, 98%, or 99% identical to such domains) are expected to be useful in forming combinations with domains from other Cry toxins to provide new toxins with increased spectrum of pest toxicity, improved potency, or increased protein stability. Domain I of the DIG-305 protein comprises approximately amino acid residues 1 to 320 of SEQ ID NO:2. Domain II of the DIG-305 protein comprises approximately amino acid residues 321 to 525 of SEQ ID NO:2. Domain III of the DIG-305 protein comprises approximately amino acid residues 526 to 685 of SEQ ID NO:2. Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding, and Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., 1996) and guidance exists on the design of the Cry toxin domain swaps (Knight et al., 2004).

Methods for generating recombinant proteins and testing them for pesticidal activity are well known in the art (see, for example, Naimov et al., 2001; de Maagd et al., 1996; Ge et al., 1991; Schnepf et al., 1990; Rang et al., 1999). Domain I from Cry1A and Cry3A proteins has been studied for the ability to insert and form pores in membranes. α-helices 4 and 5 of Domain I play key roles in membrane insertion and pore formation (Walters et al., 1993; Gazit et al., 1998; Nunez-Valdez et al., 2001), with the other helices proposed to contact the membrane surface like the ribs of an umbrella (Bravo et al., 2007; Gazit et al., 1998).

DIG-305 Variants Created by Making a Limited Number of Amino Acid Deletions, Substitutions, or Additions Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention includes insecticidal active variants of the core toxin (approximately amino acids 1 to 685 of SEQ ID NO:2), in which up to 10, up to 15, or up to 20 amino acid additions, deletions, or substitutions have been made.

The invention includes DIG-305 insecticidal toxin variants having a core toxin segment that is 90%, 91%, 92%, 93, 94%, 95%, 96%, 97%, 98%, or 99% identical to amino acids 1 to 685 of SEQ ID NO:2. Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Class of Amino Acid | Examples of Amino Acids |
|---|---|
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See, for example, U.S. Pat. No. 7,058, 515; Larson et al. (2002); Stemmer (1994a, 1994b, 1995) and Crameri et al. (1996a, 1996b, 1997). U.S. Pat. No. 8,513,492 B2

Nucleic Acids

Isolated nucleic acids encoding DIG-305 insecticidal toxins are one aspect of the present invention. This includes nucleic acids encoding SEQ ID NO:2 and complements thereof, as well as other nucleic acids that encode insecticidal variants of SEQ ID NO:2. The term "isolated" is defined herein above. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Gene Synthesis

Genes encoding the DIG-305 insecticidal toxins described herein can be made by a variety of methods well-known in the art. For example, synthetic gene segments and synthetic genes can be made by phosphite tri-ester and phosphoramidite chemistry (Caruthers et al., 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding DIG-305 insecticidal toxins can be made for example, by synthetic construction by methods currently practiced by any of several commercial suppliers. (e.g. U.S. Pat. No. 7,482,119). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-305 insecticidal toxin, a coding sequence can be designed by reverse translating the coding sequence using synonymous codons preferred by the intended host, and then refining the sequence using alternative synonymous codons to remove sequences that might cause problems in transcription, translation, or mRNA stability. Further, synonymous codons may be employed to introduce stop codons in the non-DIG-305 reading frames (i.e. reading frames 2, 3, 4, 5 and 6) to eliminate spurious long open reading frames.

Quantifying Polypeptide or Nucleic Acid Sequence Identity

The percent identity of two amino acid sequences or of two nucleic acid sequences is determined by first aligning the sequences for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST (Altschul et al., 1997) can be utilized to obtain gapped alignments for comparison purposes. Alternatively, PSI-Blast can be used to perform an iterated search that detects distant relationships between molecules (Altschul et al., 1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at http://emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (http://emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna. cmp scoring matrix. For amino acid sequence comparison, % identity or % similarity are determined using GAP weight of 8 and length weight of 2, and the BLOSUM62 scoring program. wNEEDLE reads two input sequences, finds the optimum alignment (including gaps) along their entire length, and writes their optimal global sequence alignment to file. The algorithm explores all possible alignments and chooses the best, using. a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts.

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the recombinant host cell. The treated cell, which comprises a treated toxin polypetide of the invention that retains the insecticidal activity, can be applied to the environment of the target pest to control for the pest.

Where the B.t. toxin gene is introduced via a suitable DNA construct, e.g., a vector, into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*. Of further interest are fungi, particularly yeast, e.g. genera *Saccharomyces, Cryptococcus, Kluyveromyces, Sporobolomyces, Rhodotorula*, and *Aureobasidium*, and of particular interest are phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces*

*veronae*, and *Aureobasidium pollulans*. Of particular interest are the pigmented microorganisms.

Isolated Toxin Polypeptides and Compositions of the Invention.

The DIG-305 insecticidal toxin polypeptides of the invention can be treated or prepared, for example, to make a formulated pesticide composition. Examples of formulated pesticide compositions include protein composition, sprayable protein composition, a bait matrix, or in other delivery systems. In one example, B.t. cells or recombinant host cells expressing a DIG-305 insecticidal toxin of the invention can cultured using standard art media and fermentation techniques. Upon completion of the fermentation cycle, the B.t. spores or other recombinant host cells and/or toxin crystals from the fermentation broth can be isolated by methods known in the art. B.t. spores or recombinant host cells also can be treated prior to being applied or formulated for application to plants. For example, isolated B.t. spores and/or toxin crystals can be chemically treated to prolong insecticidal activity and thereby include a treated polypeptide of the invention. Methods of growing B.t. toxin polypeptides in recombinant hosts and then treating the B.t. to prolong pesticidal activity are known and have been published. See, e.g., U.S. Pat. Nos. 4,695,462, and 4,695,455 and Gaertner et al., 1993.

The isolated or treated DIG-305 insecticidal toxin of the invention can be formulated into compositions of finely-divided particulate solids granules, pellets, wettable powders, dusts, aqueous suspensions or dispersions, emulsions, spray, liquid concentrate, or other insecticide formulations. These insecticide formulations are made by combining a DIG-305 insecticide polypeptide herein with adjuvants, diluents, surfactants, dispersants, inert carriers and other components to facilitate handling and application to control one or more target pests. Such formulation ingredients are known in the art, as are methods of application and methods of determining levels of the B.t. spores and/or isolated DIG-305 polypeptide crystals that provide desired insecticidal activity.

Methods for Controlling Insect Pests.

When an insect comes into contact with an effective amount of DIG-305 toxin disclosed herein, which is delivered via an insecticide composition (e.g., a formulated protein composition (s), sprayable protein composition(s), a bait matrix, transgenic plant expression, or another delivery system, the results are typically death of the insect, or the insects do not feed upon the source which makes the toxins available to the insects.

The subject protein toxins can be "applied" or provided to contact the target insects in a variety of ways. For example, the DIG-305 insecticidal toxin of the invention can be applied after being formulated with adjuvants, diluents, carriers, etc. to provide compositions in the form of finely-divided particulate solids, granules, pellets, wettable powders, dusts, aqueous suspensions or dispersions, and emulsions. Alternatively, the DIG-305 insecticidal polypeptide can be delivered by transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants.

The DIG-305 insecticidal toxin disclosed herein can be used to protect practically any type of plant from damage by an insect pest. Examples of such plants include potato, eggplant, tomato, pepper, tobacco, and other plants in the nightshade family. Other examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the DIG-305 insecticidal toxin, insecticidal protein, or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 and 5,141,131). Plants may be transformed using *Agrobacterium* technology, see U.S. Pat. No. 5,177,010, European Patent No. EP131624B1, European Patent No. EP159418B1, European Patent No. EP176112B1, U.S. Pat. No. 5,149,645, EP120516B1, U.S. Pat. Nos. 5,464,763, 4,693,976, European Patent No. EP116718B1, European Patent No. EP290799B1, European Patent No. EP320500B1, European Patent No. EP604662B1, U.S. Pat. Nos. 7,060,876, 6,037,526, 6,376,234, European Patent No. EP292435B1, U.S. Pat. Nos. 5,231,019, 5,463,174, 4,762,785, 5,608,142, and 5,159,135. Other transformation technology includes WHISKERS™ technology, see U.S. Pat. Nos. 5,302,523 and 5,464,765. Electroporation technology has also been used to transform plants, see WO1987006614, U.S. Pat. Nos. 5,472,869, 5,384,253, WO199209696, U.S. Pat. No. 6,074,877, WO1993021335, and U.S. Pat. No. 5,679,558. In addition to numerous technologies for transforming plants, the type of tissue which is contacted with the foreign genes may vary as well. Such tissue would include but would not be limited to embryogenic tissue, callus tissue type I and type II, hypocotyl, meristem, and the like. Almost all plant tissues may be transformed during dedifferentiation using appropriate techniques within the skill of an artisan.

Genes encoding DIG-305 insecticidal toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent No. EP120516B1; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as phosphinothricin Bialaphos, Kanamycin, Neomycin, G418, Bleomycin, Hygromycin, or a gene which codes for resistance or tolerance to glyphosate, methotrexate, imidazolinones, sulfonylureas and triazolopyrimidine herbicides, such as chlorosulfuron, bromoxynil, dalapon and the like. Of further interest are genes conferring tolerance to herbicides such as haloxyfop, quizalofop, diclofop, and the like, as exemplified by AAD genes (U.S. Patent Application No. 20090093366). The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831. For example, the DIG-305 insecticidal toxin of the invention can be optimized for expression in a dicot such as potato, eggplant, tomato, pepper, tobacco, and another plant in the nightshade family. The DIG-305 insecticidal toxin of the invention can also be optimized for expression in other dicots, or in monocots such as *Zea mays* (corn). Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g. actin, ubiquitin, CaMV 35S). Tissue specific promoters are responsible for gene expression in specific cell or tissue types, such as the leaves or seeds (e.g. zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and polyadenylate addition signal sequences. Numerous plant-specific gene transfer vectors are known to the art.

The subject invention includes plant cells that are not totipotent (non-totipotent), plant cells that are not propagative material (for example, leaf cells in some embodiments; seed cells are excluded from some embodiments) and are incapable of differentiating into whole plants. The subject invention includes plant cells that have uses other than for regenerating into a whole plant. For example, said plant cells can be used to produce a protein (such as a DIG-305 protein of the subject invention). Thus, plant cells of the subject invention include those that have uses other than totipotency (that is, some cells of subject invention are not regenerable into a whole plant). However, some embodiments do include seed cells and plant cells that can be regenerated into a whole plant.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as Bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO2007053482), or phenoxy acids herbicides and aryloxyphenoxypropionates herbicides (see U.S. Patent Application No. 20090093366). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g. other insect resistance conferred by B.t.-derived or other insecticidal proteins, insect resistance conferred by mechanisms such as RNAi and the like, nematode resistance, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack or co-transformation). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests.

The DIG-305 insecticidal toxins of the invention are particularly suitable for use in control of insects pests. Coleopterans are one important group of agricultural, horticultural, and household pests which cause a very large amount of damage each year. This large insect order encompasses foliar- and root-feeding larvae and adults, including members of, for example, the insect families—Chrysomelidae, Coccinellidae, Curculionidae, Dermestidae, Elateridae, Scarabaeidae, Scolytidae, and Tenebrionidae. Included within these families are leaf beetles and leaf miners in the family Chrysomelidae, potato beetles (e.g. Colorado potato beetle (*Leptinotarsa decemlineata* Say), grape *colaspis* (*Colaspis brunnea* Fabricius), cereal leaf beetle (*Oulema melanopus* Linnaeus), sunflower beetle (*Zygogramma exclamahonis* Fabricius), and beetles in the family Coccinellidae (e.g. Mexican bean beetle (*Epilachna varivestis* Mulsant)). Further examples are chafers and other beetles in the family Scarabaeidae (e.g. Japanese beetle (*Popillia japonica* Newman), northern masked chafer (white grub, *Cyclocephala borealis* Arrow), southern masked chafer (white grub, *Cyclocephala immaculata* Olivier), European chafer (*Rhizotrogus majalis* Razoumowsky), white grub (*Phyllophaga crinita* Burmeister), carrot beetle (*Ligyrus gibbosus* De Geer), and chafers of the genera *Holotrichia* spp and *Melolontha* spp.). Further examples of coleopteran insects are weevils (e.g. boll weevil (*Anthonomus grandis* Boheman), rice water weevil (*Lissorhoptrus oryzophilus* Kuschel), granary weevil (*Sitophilus grananus* Linnaeus), rice weevil (*Sitophilus oryzae* Linnaeus), and clover leaf weevil (*Hypera punctata* Fabricius)). Also included are maize billbug (*Sphenophorus maidis* Chittenden), flea beetles (e.g. corn flea beetle (*Chaetocnema pulicara* Melsheimer), and crucifer flea beetle (*Phyllotreta cruciferae* Goeze)), spotted cucumber beetle (*Diabrotica undecimpunctata*), and rootworms, (e.g. western corn rootworm (*Diabrotica virgifera virgifera* LeConte), northern corn rootworm (*Diabrotica barben* Smith & Lawrence), the Mexican corn rootworm ((MCR) *D. virgifera zeae* Krysan and Smith), *D. balteata* LeConte, *D. undecimpunctata* tenella, *D. u. undecimpunctata* Mannerheim, and southern corn rootworm (*Diabrotica undecimpunctata howardi* Barber)). Further examples of coleopteran pests are beetles of the family Rutelinae (shining leaf chafers) such as the genus *Anomala* (including *A. marginata, A. lucicola, A. oblivia* and *A. orientalis*). Additional coleopteran insects are carpet beetles from the family Dermestidae, wireworms from the family Elateridae (e.g. *Melanotus* spp., *Conoderus* spp., *Limonius* spp., *Agriotes* spp., *Ctenicera* spp., *Aeolus* spp.)), bark beetles from the family Scolytidae, and beetles from the family Tenebrionidae (e.g. *Eleodes* spp). Any genus listed above (and others), generally, can also be targeted as a part of the subject invention by insecticidal compositions including DIG-305 insecticidal polypeptide alone or in combination with another insecticidal agent. Any additional insects in any of these genera (as targets) are also included within the scope of this invention.

Use of DIG-305 insecticidal toxins to control coleopteran pests of crop plants is contemplated. In some embodiments, Cry proteins may be economically deployed for control of insect pests that include but are not limited to, for example, rootworms such as western corn rootworm (*Diabrotica virgifera virgifera* LeConte), northern corn rootworm (*Diabrotica barberi* Smith & Lawrence), and southern corn rootworm (*Diabrotica undecimpunctata howardi* Barber), and grubs such as the larvae of *Cyclocephala borealis* (northern masked chafer), *Cyclocephala immaculate* (southern masked chafer), and *Popillia japonica* (Japanese beetle).

Lepidopterans are another important group of agricultural, horticultural, and household pests which cause a very large amount of damage each year. The invention provides use of DIG-305 toxins in combination with other insecticides to control insect pests within this order by is within the scope of this invention. This insect order encompasses foliar- and root-feeding larvae and adults, including members of, for example, the insect families Arctiidae, Gelechiidae, Geometridae, Lasiocampidae, Lymantriidae, Noctuidae, Pyralidae, Sesiidae, Sphingidae, Tineidae, and Tortricidae. Lepidopteran insect pests include, but are not limited to: *Achoroia grisella, Acleris gloverana, Acleris variana, Adoxophyes orana, Agrotis ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens* (tobacco budworm), *Hemileuca oliviae, Homoeosoma electellum, Hyphantia cunea, Keiferia lycopersicella, Lambdina fiscellaria fiscellaria, Lambdina fis-*

*cellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia ni,* (cabbage looper), *Udea rubigalis, Xylomyges curiails,* and *Yponomeuta padella.*

Use of the DIG-305 insecticidal toxins to control parasitic nematodes including, but not limited to, root knot nematode (*Meloidogyne incognita*) and soybean cyst nematode (*Heterodera glycines*) is also contemplated.

Anti-Toxin Antibodies

Antibodies to the toxins disclosed herein, or to equivalent toxins, or fragments of these toxins, can readily be prepared using standard procedures in this art. Such antibodies are useful to detect the presence of the DIG-305 toxins using standard ELISA methods.

Detection Using Probes.

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization.

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(°\ C.)=81.5°\ C.+16.6(\log M)+0.41(\%\ GC)-0.61(\%\ \text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983).

$$T_m(°\ C.)=81.5°\ C.+16.6(\log[Na+])+0.41(\%\ GC)-0.61(\%\ \text{formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995). Also see Sambrook et al. (1989).

Hybridization of immobilized DNA on Southern blots with radioactively labeled gene-specific probes may be performed by standard methods (Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20° C. to 25° C. below the $T_m$ of the DNA hybrid in 6×SSPE, 5×Denhardt's Solution, 0.1% SDS, 0.1 mg/mL denatured DNA (20×SSPE is 3M NaCl, 0.2 M NaHPO$_4$, and 0.02M EDTA (ethylenediamine tetra-acetic acid sodium salt); 100× Denhardt's Solution is 20 gm/L Polyvinylpyrollidone, 20 gm/L Ficoll type 400 and 20 gm/L Bovine Serum Albumin (fraction V)).

Washes may typically be carried out as follows: Twice at room temperature for 15 minutes in 1×SSPE, 0.1% SDS (low stringency wash). Once at $T_m$–20° C. for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(° C.)=2(\text{number of } T/A \text{ base pairs})+4(\text{number of } G/C \text{ base pairs})$$

Washes may typically be carried out as follows: Twice at room temperature for 15 minutes 1×SSPE, 0.1% SDS (low stringency wash). Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

All patents, patent applications, provisional applications, and publications referred to or cited herein are incorporated by reference in their entirety to the extent they are not inconsistent with the explicit teachings of this specification.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

Unless specifically indicated or implied, the terms "a", "an", and "the" signify "at least one" as used herein.

All percentages are by weight and all solvent mixture proportions are by volume unless otherwise noted. All temperatures are in degrees Celsius.

Example 1

Isolation of a Gene Encoding DIG-305 Toxin

Unless otherwise indicated, molecular biological and biochemical manipulations described in this and subsequent Examples were performed by standard methodologies as disclosed in, for example, Ausubel et al. (1995), and Sambrook et al. (1989), and updates thereof. Nucleic acid encoding the insecticidal Cry protein designated herein as DIG-305 was isolated from B.t. strain PS18A also known as DBt10340. Degenerate Forward and Reverse primers for Polymerase Chain Reactions (PCR) were designed and used to amplify a DNA fragment with homology to Cry32 from genomic DNA library. The determined sequence of the amplified fragment was used for genome walking to obtain the complete open reading frame of DIG-305. SEQ ID NO:1 is the 3726 bp nucleotide sequence encoding the full length DIG-305 protein. SEQ ID NO:2 is the 1241 amino acid sequence of the full length DIG-305 protein deduced from SEQ ID NO:1.

Example 2

DIG-305 Chimeric Toxin in Bacterial Hosts

Standard cloning methods are used in the construction of *Pseudomonas fluorescens* (Pf) expression plasmids engineered to produce DIG-305 chimera toxin consisting of the DIG-305 core toxin encoding sequence (encoding amino acids 1-685) and the Cry1Ab protoxin encoding segment as described above, each encoded by the maize-optimized coding sequences. Restriction endonucleases are obtained from New England BioLabs (NEB; Ipswich, Mass.) and T4 DNA Ligase (Invitrogen) are used for DNA ligation. Plasmid preparations are performed using the NucleoSpin® Plasmid Kit (Macherey-Nagel Inc, Bethlehem, Pa.) following the instructions of the supplier. DNA fragments are purified using the QIAquick Gel Extraction kit (Qiagen) after agarose Tris-acetate gel electrophoresis. The linearized vector is phosphatased with NEB Antarctic Phosphatase to enhance formation of recombinant molecules.

The basic cloning strategy entailed subcloning a DNA fragment having the DIG-305 Cry1Ab chimera coding sequence (CDS) into pDOW1169 at, for example, SpeI and SalI restriction sites, whereby the DIG-305 chimera CDS is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). The expression plasmids are transformed by electroporation into DC454 (a near wild-type *P. fluorescens* strain having mutations ΔpyrF and lsc::lacIQI), or its derivatives, recovered in SOC-Soy hydrolysate medium, and plated on selective medium (M9 glucose agar lacking uracil, Sambrook et al., supra). Details of the transformation and selection methods are generally described available in Squires et al. (2004), U.S. Patent Application No. 20060008877, U.S. Pat. No. 7,681,799, and U.S. Patent Application No. 20080058262, incorporated herein by reference. Recombinant colonies are identified by restriction digestion of miniprep plasmid DNA.

Production of DIG-305 chimera for characterization and insect bioassay is accomplished by shake-flask-grown *P. fluorescens* strains harboring expression constructs. Seed cultures grown in M9 medium supplemented with glucose and trace elements are used to inoculate defined minimal medium. Expression of the DIG-305 chimera coding sequences are induced by addition of isopropyl-β-D-1-thiogalactopyranoside (IPTG) after an initial incubation of 24 hours at 30° C. with shaking. Cultures are sampled at the time of induction and at various times post-induction. Cell density is measured by optical density at 600 nm ($OD_{600}$). Other culture media suitable for growth of *Pseudomonas fluorescens* may also be utilized, for example, as described in Huang et al. 2007 and U.S. Patent Application No. 20060008877 in cells from *P. fluorescens* fermentations that produced insoluble B.t. insecticidal protein inclusion bodies (IB). Briefly, cells are lysed, pellet and supernatant fractions are prepared by centrifugation, The pellet is resuspended and repeatedly washed by resuspension in lysis buffer until the supernatant becomes colorless and the IB pellet becomes firm and off-white in color. The final pellet is washed, resuspended in sterile-filtered distilled water containing 2 mM EDTA, and stored at −80° C. The supernatant fraction is enriched for the recombinant protein by column chromatography.

Preparations are analyzed by SDS-PAGE. Quantification of target bands is done by comparing densitometric values for the bands against Bovine Serum Albumin (BSA) samples run on the same gel to generate a standard curve. The sample buffer is then changed to 10 mM CAPS (3-(cyclohexamino) 1-propanesulfonic acid) pH10, using disposable PD-10 columns (GE Healthcare, Piscataway, N.J.).

The concentrated extract is analyzed and quantified by SDS-PAGE relative to background-subtracted BSA standards to generate a standard curve to calculate the concentration of DIG-305 chimera.

Example 3

Design of a Plant-Optimized Coding Sequence for the DIG-305 B.t. Insecticidal Toxin One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias is designed and synthesized to produce a DIG-305 insecticidal protein in transgenic monocot plants. A codon usage table for maize (*Zea mays* L.) was calculated from hundreds of protein coding sequences obtained from sequences deposited in GenBank (www.ncbi.nlm.nih.gov). A rescaled maize codon set was calculated after omitting any synonymous codon used less than about 10% of total codon uses for that amino acid.

To derive a maize-codon-optimized DNA sequence encoding the DIG-305 protein core toxin of SEQ ID NO:3, or insecticidal fragments thereof, or DIG-305 chimera toxins, are the subject of codon substitutions to the experimentally determined (native) DIG-305 DNA sequence (SEQ ID NO:1) encoding the toxin were made such that the resulting DNA sequence had the overall codon composition of the maize-optimized codon bias table. Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased Rescaled codon composition. A maize-optimized DNA sequence encoding DIG-305 core toxin is disclosed as SEQ ID NO:3.

Example 4

Construction of Expression Plasmid Encoding the DIG-305 Toxin in Bacterial Hosts Standard cloning methods were used in the construction of *Pseudomonas fluorescens* (Pf) expression plasmids engineered to produce DIG-305 encoded by the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAquick Gel Extraction kit (Qiagen) after agarose Tris-acetate gel electrophoresis. The linearized vector was phosphatased with NEB Antarctic Phosphatase to enhance formation of recombinant molecules.

A DNA fragment having the DIG-305 coding sequence (CDS), as provided by SEQ ID NO:3, was subcloned into pDOW1169 at, for example, SpeI and SalI restriction sites, whereby the DIG-305 CDS was placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). The expression plasmid (pDAB107162, containing the DIG-305 coding sequence) was transformed by electroporation into DC454 (a near wild-type *P. fluorescens* strain having mutations ΔpyrF and lsc::lacIQI), or derivatives thereof, recovered in SOC-Soy hydrolysate medium, and plated on selective medium (M9 glucose agar lacking uracil, Sambrook et al., supra). The transformation and selection methods are generally described available in Squires et al. (2004), U.S. Patent Application No. 20060008877, U.S. Pat. No. 7,681, 799, and U.S. Patent Application No. 20080058262, incorporated herein by reference. Recombinant colonies were identified by restriction digestion of miniprep plasmid DNA.

The resulting expression strain is known as DPf21990 in the Dow AgroSciences Recombinant Culture Collection.

Example 5

Preparation of DIG-305 Protein Samples

Production of DIG-305 for characterization and insect bioassay was accomplished by expression of DIG-305 in shake-flask-grown *P. fluorescens* strain DPf21990 which harbors expression plasmid pDAB107162. Seed cultures grown in M9 medium supplemented with glucose and trace elements were used to inoculate defined minimal medium with 5% glycerol (Teknova Cat. #3D7426, Hollister, Calif.). Expression of the DIG-305 coding region was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. 2007 and U.S. Patent Application No. 20060008877. Briefly, cells are lysed, IB pellet is collected by centrifugation, IB is resuspended and repeatedly washed by resuspension in lysis buffer until the supernatant becomes colorless and the IB pellet becomes firm and off-white in color. The final pellet is washed, resuspended in sterile-filtered distilled water containing 2 mM EDTA, and stored at −80° C.

IB preparations are analyzed by SDS-PAGE. Quantification of target bands is done by comparing densitometric values for the bands against Bovine Serum Albumin (BSA) samples run on the same gel to generate a standard curve. Target protein is subsequently extracted from the inclusion body using sodium carbonate buffer and gently rocking on a platform at 4° C. overnight. Solubilized DIG-305 is centrifuged and the resulting supernatant is concentrated. The sample buffer is then changed to 10 mM CAPS (3-(cyclohexamino)1-propanesulfonic acid) pH10, using disposable PD-10 columns (GE Healthcare, Piscataway, N.J.).

The concentrated extract is analyzed and quantified by SDS-PAGE relative to background-subtracted BSA standards to generate a standard curve to calculate the concentration of DIG-305.

Example 6

Insect Activity of DIG-305 Insecticidal Toxin

DIG-305 was tested and found to have insecticidal activity on larvae of the coleopteran insect, the Western corn rootworm (*Diabrotica virgifera virgifera*).

A solution containing purified proteins (either solubilized or as inclusion bodies; Table 2) were tested for insecticidal activity in bioassays conducted with Western corn rootworm (*Diabrotica virgifera virgifera*) larvae. Insect eggs were received from CROP CHARACTERISTICS, INC. (Farmington, Minn.).

*D. virgifera virgifera* bioassays were conducted in 128-well bioassay trays and a Dow AgroSciences LLC proprietary rootworm diet was used and 80 to 100 µl of aliquot solution was used to treat the diet surface. The treated trays were air dried, and one individual larva was deposited on the treated diet surface. The infested wells were then sealed with adhesive sheets of clear plastic vented to allow gas exchange (C-D International, Pitman, N.J.). Bioassay trays were held under controlled environmental conditions (28° C., 40% relative humidity, 16:8 h light:dark photoperiod) for 5 days. The total number of insects exposed to each protein sample, the number of dead insects, and the weight of surviving insects were recorded in all bioassays. Trypsin activated Cry3Aa was used as a positive control. Negative controls included water; untreated; Cry1Fa; 20 mM NaCitrate, p.H. 3.5; and 10 mM CAPS, pH 10.

Percent mortality and percent growth inhibition were calculated for each treatment. Growth inhibition (GI) is calculated as follows:

$$GI = [1 - (TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Bioassay results are summarized in Table 2 below. Replicated bioassays demonstrated that ingestion of DIG-305 preparations caused mortality and growth inhibition of Western corn rootworm (Table 2).

TABLE 2

| Treatment | Dose (ug/cm2) | N | Average % Mortality | St. Dev. (%) | Average GI | St. Dev. |
|---|---|---|---|---|---|---|
| DIG-305 | 300 | 4 | 90.0 | 12.25 | 0.964 | 0.042 |
| Cry3Aa (Positive Control) | 350 | 2 | 80.6 | 0.85 | 0.902 | 0.111 |
| Water | 0 | 2 | 7.7 | 12.87 | NA | NA |
| Buffer 10 mM CAPS pH 10 (Negative Control) | 0 | 2 | 7.3 | 10.11 | NA | NA |
| 20 mM NaCitrate, p.H. 3.5 (Negative Control) | 0 | 2 | 15.0 | 7.07 | NA | NA |
| Cry1Fa (Negative Control) | 350 | 2 | 33.3 | 17.68 | 0.372 | 0.196 |
| Untreated | 0 | 2 | 47.4 | 6.22 | NA | NA |

DIG-305 protein from inclusion bodies solubilized (10 mM CAPS pH 10) and tested against Western corn rootworm.

Example 7

*Agrobacterium* Transformation

Standard cloning methods are used in the construction of binary plant transformation and expression plasmid. Restriction endonucleases and T4 DNA Ligase are obtained from NEB. Plasmid preparations are performed using the NucleoSpin® Plasmid Preparation kit or the NucleoBond® AX Xtra Midi kit (both from Macherey-Nagel), following the instructions of the manufacturers. DNA fragments are purified using the QIAquick PCR Purification Kit or the QIAEX II Gel Extraction Kit (both from Qiagen) after gel isolation.

DNA comprising a nucleotide sequence that encodes a DIG-305 insecticidal toxin is synthesized by a commercial vendor (e.g. DNA2.0, Menlo Park, Calif.) and supplied as cloned fragments in a plasmid vector. Other DNA sequences encoding other DIG-305 toxins are obtained by standard molecular biology manipulation of constructs containing appropriate nucleotide sequences. The DNA fragments encoding the modified DIG-305 fragments are joined to other DIG-305 insecticidal toxin coding region fragments or other B.t. (Cry) coding region fragments at appropriate restriction sites to obtain a coding region encoding the desired full-length DIG-305 toxin protein.

Full length or modified coding sequences (CDS) for DIG-305 insecticidal toxin is subcloned into a plant expression plasmid at NcoI and SacI restriction sites. The resulting plant expression cassettes containing the appropriate Cry coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full length and modified gene plant expression cassettes into a binary plant transformation plasmid if the Gateway® technology is utilized. The binary plant transformation vector includes a bacterial selectable marker gene that confers resistance to the antibiotic spectinomycin when the plasmid is present in E. coli and Agrobacterium cells. The binary vector plasmid also includes a plant-expressible selectable marker gene that is functional in the desired host plants, namely, the aminoglycoside phosphotransferase gene of transposon Tn5 (aphII) which encodes resistance to the antibiotics Kanamycin, Neomycin and G418.

Electro-competent cells of Agrobacterium tumefaciens strain Z707S (a streptomycin-resistant derivative of Z707; Hepburn et al., 1985) are prepared and transformed using electroporation (Weigel and Glazebrook, 2002). After electroporation, 1 mL of YEP broth (gm/L: yeast extract, 10; peptone, 10; NaCl, 5) are added to the cuvette and the cell-YEP suspension is transferred to a 15 mL culture tube for incubation at 28° C. in a water bath with constant agitation for 4 hours. The cells are plated on YEP plus agar (25 gm/L) with spectinomycin (200 µg/mL) and streptomycin (250 µg/mL) and the plates are incubated for 2-4 days at 28° C. Well separated single colonies are selected and streaked onto fresh YEP+agar plates with spectinomycin and streptomycin, and incubated at 28° C. for 1-3 days.

The presence of the DIG-305 insecticidal toxin gene insert in the binary plant transformation vector is performed by PCR analysis using vector-specific primers with template plasmid DNA prepared from selected Agrobacterium colonies. The cell pellet from a 4 mL aliquot of a 15 mL overnight culture grown in YEP with spectinomycin and streptomycin as before is extracted using Qiagen Spin Mini Preps, performed per manufacturer's instructions. Plasmid DNA from the binary vector used in the Agrobacterium electroporation transformation is included as a control. The PCR reaction is completed using Taq DNA polymerase from Invitrogen per manufacturer's instructions at 0.5× concentrations. PCR reactions are carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction is maintained at 4° C. after cycling. The amplification products are analyzed by agarose gel electrophoresis (e.g. 0.7% to 1% agarose, w/v) and visualized by ethidium bromide staining. A colony is selected whose PCR product is identical to the plasmid control.

Another binary plant transformation vector containing the DIG-305 insecticidal toxin gene insert is performed by restriction digest fingerprint mapping of plasmid DNA prepared from candidate Agrobacterium isolates by standard molecular biology methods well known to those skilled in the art of Agrobacterium manipulation.

Example 8

Production of DIG-305 Insecticidal Toxins in Dicot Plants

Arabidopsis Transformation

Arabidopsis thaliana Col-01 is transformed using the floral dip method (Weigel and Glazebrook, 2002). The selected Agrobacterium colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: 1/2× Murashige and Skoog salts (Sigma-Aldrich)/Gamborg's B5 vitamins (Gold Bio-Technology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

Arabidopsis Growth and Selection

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Anton, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 µmol/m$^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of Transgenic *Arabidopsis*

Transgenic *Arabidopsis* lines expressing DIG-305 insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

Example 9

*Agrobacterium* Transformation for Generation of Superbinary Vectors

The *Agrobacterium* superbinary system is conveniently used for transformation of monocot plant hosts. Methodologies for constructing and validating superbinary vectors are well established. See, for example, European Patent No. EP604662B1 and U.S. Pat. No. 7,060,876. Standard molecular biological and microbiological methods are used to generate superbinary plasmids. Verification/validation of the structure of the superbinary plasmid is done using methodologies as described above for binary vectors.

Example 10

Production of DIG-305 Insecticidal Toxins in Monocot Plants

*Agrobacterium*-Mediated Transformation of Maize Seeds from a Hi-II $F_1$ cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution is vortexed until a uniform suspension is achieved, and the concentration is adjusted to a final density of 200 Klett units, using a Klett-Summerson colorimeter with a purple filter, or an equivalent optical density measured at 600 nm ($OD_{600}$). Immature embryos are isolated directly into a micro centrifuge tube containing 2 mL of the infection medium. The medium is removed and replaced with 1 mL of the *Agrobacterium* solution with a density of 200 Klett units or equivalent $OD_{600}$, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 μM acetosyringone, 3.0 gm/L Gellan gum (PhytoTechnology Laboratories., Lenexa, Kans.), pH 5.8) for 5 days at 25° C. under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates are obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and Seed Production

For regeneration, the cultures are transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they are transferred to glass culture tubes containing SHGA medium (Schenk and Hildebrandt (1972) salts and vitamins); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

Example 11

Bioassay of Transgenic Maize

Bioactivity of the DIG-305 insecticidal toxins produced in plant cells is demonstrated by conventional bioassay methods (see, for example Huang et al., 2006). One is able to demonstrate efficacy, for example, by feeding various plant tissues or tissue pieces derived from a plant producing a DIG-305 insecticidal toxin to target insects in a controlled feeding environment. Alternatively, protein extracts may be prepared from various plant tissues derived from a plant producing the DIG-305 insecticidal toxin and the extracted proteins incorporated into artificial diet bioassays as previously described herein. It is to be understood that the results of such feeding assays are to be compared to similarly conducted bioassays that employ appropriate control tissues from host plants that do not produce a DIG-305 insecticidal toxin, or to other control samples.

REFERENCES

An, G., Watson, B. D., Stachel, S., Gordon, M. P., Nester, E. W. (1985) New cloning vehicles for transformation of higher plants. EMBO J. 4:277-284.

Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schaffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillus thuringiensis* for lepidopteran larvae: factors involved in vivo and in the structure of a purified toxin. Molec. Microbiol. 3:1533-1543.

Ausubel et al., eds. (1995) Current Protocols in Molecular Biology, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Baum, J. A., Bogaert T., Clinton W., Heck G. R., Feldmann P., Ilagan O., Johnson S., Plaetinck G., Munyikwa T., Pleau M., Vaughn T., Roberts J., (2007) Control of coleopteran insect pests through RNA interference. Nat. Biotechnol. November; 25(11):1322-1326.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Bown, D. P., Wilkinson, H. S., Jongsma, M. A., Gatehouse, J. A. (2004) Characterization of cysteine proteinases responsible for digestive proteolysis in guts of larval western corn rootworm (*Diabrotica virgifera*) by expression in the yeast *Pichia pastoris*. Insect Biochem. Molec. Biol. 34:305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia Sinica 18:659-668.

Crameri, A., Cwirla, S., Stemmer, W. P. C. (1996a) Construction and evolution of antibody-phage libraries by DNA shuffling. Nat. Med. 2:100-103.

Crameri, A., Whitehom, E. A., Tate, E., Stemmer, W. P. C. (1996b) Improved green fluorescent protein by molecular evolution using DNA shuffling. Nat. Biotech. 14:315-319.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crickmore N., Zeigler, D. R., Feitelson J., Schnepf, E., Van Rie J., Lereclus D., Baum J., and Dean D. H. (1998) Revision of the Nomenclature for the *Bacillus thuringiensis* Pesticidal Crystal Proteins Microbiol. Mol. Biol. Reviews 62:807-813.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Ellis, R. T., Stockhoff, B. A., Stamp, L., Schnepf, H. E., Schwab, G. E., Knuth, M., Russell, J., Cardineau, G. A., Narva, K. E. (2002) Novel *Bacillus thuringiensis* binary insecticidal crystal proteins active on western corn rootworm, *Diabrotica virgifera virgifera* LeConte. Appl. Environ. Microbiol. 68:1137-1145.

Englemann, F., Geraerts, W. P. M., (1980) The proteases and the protease inhibitor in the midgut of *Leucophaea maderae*. J. Insect Physiol. 261:703-710.

Fraley, R. T., Rogers, S. G., Horsch, R. B. (1986) Genetic transformation in higher plants. Crit. Rev. Plant Sci. 4:1-46.

Frankenhuyzen, K., (2009) Insecticidal activity of *Bacillus thuringiensis* crystal proteins. J. of Invertebrate Pathology. 101(1):1-16.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on CryIA(c). J. Biol. Chem. 266: 17954-17958.

Gillikin, J. W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Haider, M. Z., Knowles, B. H., Ellar, D. J. (1986) Specificity of *Bacillus thuringiensis* var. colmeri insecticidal δ-endotoxin is determined by differential proteolytic processing of the protoxin by larval gut proteases. Eur. J. Biochem. 156:531-540.

Heckel, D. G., Gahan, L. J., Baxter, S. W., Zhao, J-Z., Shelton, A. M., Gould, F., Tabashnik, B. E. (2007) The diversity of Bt resistance genes in species of Lepidoptera. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131:2961-2969.

Hoagland, D. R., Arnon, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) Structural and functional analysis of a cloned delta endotoxin of *Bacillus thuringiensis* berliner 1715. Eur. J. Biochem. 161:273-280.

Honée, G., Convents, D., Van Rie, J., Jansens, S., Peferoen, M., Visser, B. (1991) The C-terminal domain of the toxic fragment of a *Bacillus thuringiensis* crystal protein determines receptor binding. Mol. Microbiol. 5:2799-2806

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272:1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K, D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Linsmaier, E. M., Skoog, F. (1965) Organic growth factor requirements of tobacco tissue. Physiologia Plantarum 18:100-127.

Littlefield, J. W. (1964) Selection of hybrids from matings of fibroblasts in vitro and their presumed recombinants. Science 145:709-710.

Meinkoth, J., Wahl, G. (1984) Hybridization of nucleic acids immobilized on solid supports. Anal. Biochem. 138:267-284.

Metcalf, R. L. (1986) The ecology of insecticides and the chemical control of insects. pp. 251-297. In (Marcos Kogan (ed.)) Ecological theory and integrated pest management practice. John Wiley & Sons, N. Y. 362 pp.

Moellenbeck, D. J., Peters, M. L., Bing, J. W., Rouse, J. R., Higgins, L. S., Sims, L., Nevshemal, T., Marshall, L., Ellis, R. T., Bystrak, P. G., Lang, B. A., Stewart, J. L., Kouba, K., Sondag, V., Gustafson, V., Nour, K., Xu, D., Swenson, J., Zhang, J., Czapla, T., Schwab, G., Jayne, S., Stockhoff, B. A., Narva, K., Schnepf, H. E., Stelman, S. J., Poutre, C., Koziel, M., Duck, N. (2001) Insecticidal proteins from *Bacillus thuringiensis* protect corn from corn rootworms. Nat. Biotech. 19:668-672.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado potato beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim. Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun. 362:437-442.

Pigott, C. R., Ellar, D. J. (2007) Role of receptors in *Bacillus thuringiensis* crystal toxin activity. Microbiol. Molec. Biol. Rev. 71:255-281.

Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Sambrook, J., Fritsch, E. F., Maniatis, T. (1989) Molecular Cloning: A Laboratory Manual (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified Bt toxins to counter insect resistance. Science 318:1640-1642.

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encyclopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown (ed.), Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to Bt crops: evidence versus theory. Nat. Biotech. 26:199-202.

Taggart, R. T., Samloff, I. M. (1983) Stable antibody-producing murine hybridomas. Science 219:1228-1230.

Thie, N. M. R., Houseman J. G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Varshaysky, A. (1997) The N-end rule pathway of protein degradation. Genes to Cells 2:13-28.

Vaughn, T., Cavato, T., Brar, G., Coombe, T., DeGooyer, T., Ford, S., Groth, M., Howe, A., Johnson, S., Kolacz, K., Pilcher, C., Prucell, J., Romano, C., English, L., Pershing, J. (2005) A method of controlling corn rootworm feeding using a *Bacillus thuringiensis* protein expressed in transgenic maize Crop. Sci. 45:931-938.

Walters, F. S., Slatin, S. L., Kulesza, C. A., English, L. H. (1993) Ion channel activity of N-terminal fragments from CryIA(c) delta-endotoxin. Biochem. Biophys. Res. Commun 196:921-926.

Walters, F. S., Stacy, C. M., Lee, M. K., Palekar, N., Chen, J. S. (2008) An engineered chymotrypsin/cathepsin G site in domain I renders *Bacillus thuringiensis* Cry3A active against western corn rootworm larvae. Appl. Environ. Microbiol. 74:367-374.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. (eds.) (2002) *Arabidopsis*: A Laboratory Manual. Cold Spring Harbor Press, Cold Spring Harbor, N.Y., 354 pages.

Witkowski, J. F., Wedberg, J. L., Steffey, K. L., Sloderbeck, P. E., Siegfried, B. D., Rice, M. E., Pilcher, C. D., Onstad, D. W., Mason, C. E., Lewis, L. C., Landis, D. A., Keaster, A. J., Huang, F., Higgins, R. A., Haas, M. J., Gray, M. E., Giles, K. L., Foster, J. E., Davis, P. M., Calvin, D. D., Buschman, L. L., Bolin, P. C., Barry, B. D., Andow, D. A., Alstad, D. N. (2002) Bt corn and European Corn Borer (Ostlie, K. R., Hutchison, W. D., Hellmich, R. L. (eds)). University of Minnesota Extension Service. Publ. WW-07055.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

We claim:

1. An isolated, treated, or formulated dig-305 insecticidal toxin polypeptide comprising a core toxin segment that includes an amino acid sequence selected from the group consisting of:
    (a) residues 2 to 685 of SEQ ID NO:2; and
    (b) a sequence having at least 99% sequence identity to the amino acid sequence of residues 2 to 685 of SEQ ID NO:2;
    wherein the core toxin segment is linked to a C-terminal protoxin portion of a Cry toxin other than DIG-305.

2. The isolated, treated, or formulated polypeptide of claim 1, wherein the polypeptide is a chimeric protein and the C-terminal protoxin portion comprises the C-terminal protoxin portion of cry1Ab or a cry1Ac/cry1Ab chimeric toxin.

3. The isolated, treated, or formulated polypeptide of claim 2, wherein the C-terminal protoxin portion comprises the C-terminal protoxin portion of Cry1Ab.

4. The isolated, treated, or formulated polypeptide of claim 2, wherein the C-terminal protoxin portion comprises the C-terminal protoxin portion of cry1Ac/cry1Ab chimeric toxin.

5. A method for controlling a pest population, said method comprising contacting said population with a pesticidally effective amount of the polypeptide of claim 1.

6. The polypeptide of claim 1 having activity against a coleopteran pest.

7. The polypeptide of claim 1 having activity against corn rootworm.

8. A composition comprising the polypeptide of claim 1.

9. The composition of claim 8, wherein the composition is a sprayable protein composition, encapsulated protein composition, or bait matrix that comprises a formulated DIG-305 insecticidal toxin.

10. A nucleic acid construct, wherein the construct comprises a heterologous nucleic acid sequence that is recombinantly linked to a sequence encoding a DIG-305 insecticidal toxin comprising a core toxin segment that includes an amino acid sequence selected from the group consisting of:
    (a) residues 2 to 685 of SEQ ID NO:2; and
    (b) a sequence having at least 99% sequence identity to the amino acid sequence of residues 2 to 685 of SEQ ID NO:2.

11. The nucleic acid construct of claim 10, wherein the heterologous nucleic acid sequence is a promoter sequence capable of driving expression in a plant.

12. The nucleic acid construct of claim 10, wherein the sequence encoding the polypeptide is codon-optimized for expression in a plant.

13. The nucleic acid construct of claim 11, wherein the promoter is capable of driving expression in corn and the sequence encoding the polypeptide is codon optimized for expression in corn.

14. The nucleic acid construct of claim 10, wherein the sequence encoding the polypeptide comprises SEQ ID NO:1 or SEQ ID NO:3.

15. The nucleic acid construct of claim 13, wherein the construct is a vector and the vector comprises SEQ ID NO:3.

16. The nucleic acid construct of claim 11, wherein the promoter is capable of driving expression in potato and the sequence encoding the polypeptide is codon optimized for expression in potato.

17. A transgenic plant comprising the nucleic acid construct of claim 10 stably incorporated into its genome.

18. A method for protecting a plant from a pest, said method comprising introducing into said plant the construct of claim 10.

* * * * *

SEQUENCE LISTING

<160> NUMBER OF SEQ ID NOS: 3

<210> SEQ ID NO 1
<211> LENGTH: 3726
<212> TYPE: DNA
<213> ORGANISM: Bacillus thuringiensis

<400> SEQUENCE: 1

```
atgaatcaga attacaatga atatgaaatt ctaggtactg gtggtatggg ctatcagtca      60
agatatccac ttgcgaaaga accaggttca gaattgcaac aaatgagtta taaggattgg     120
atggataggt gtgaacgagg gtcgctggca atcacattta aatccgttat tacaaccgct     180
```

```
ttagatatta cgtctgcaat cctcggtgcg gcaaaatctc caaaagctaa agtagcaaga    240
gctgcagttc aagtccttaa tgccgttatt aaattgctgt ggcctgaacc agagaaacct    300
tctgaaccag catacgatat agatttcata tggaaagaac tgatagagag agtcgaaata    360
ctgattgaag aaaaaattga ccaagaagct ataacgccg cagttggaag attatcagga     420
ttaaagagag ctttaaattt atatcaaata tcgtttgagc tttgggttga agatgaaaat    480
gaccctgagt tacaggaaga tatacgaact cggtttacgt ctgcactgtt tgaacttgtg    540
actacaattg aaacatttaa atacaatgga caagagttaa atttactgac cgttttttgta   600 caagctgcag attttcactt aatgttatta caacaagggg taatgtatgg agttcgttgg    660
ggattcgatc agagaacggt agattctttt taccaaaatg acagaggaga aggtttaaaa    720
gatttgctaa cgaagtattc tgattatgcc acatattggt atggagaagg tttgaataga    780
gcaaaaaact tgaaggcaaa tttatcagat acattaagat atccttgggc cgcaaactta    840
gaagatgcga gtgtattaca agagctagag gattggaacc tatataacga ttatcgaaga    900
gatatgacaa tcttagtatt agatttggtt gcggtatggc caacatatga cctccgctat    960
tacgataatg aaactatggg ggtacagtct gaactgacac gatctatata ctctcaagca   1020
gtaggaaatg taatgggaac tgtatttaca aaagagcaat acgaggttag cttcgttcgc   1080
ccaccacact tagttacatg gttagaaaaa atgtttgttc atataagaga caaagaacag   1140
ggggcaccta ttgatgcgga aatggctggt ataagtctag attattcttg ttcaggttgg   1200
gataatacgg tttatgacat acttcaagga tatccggcga ctgggggtag tcaaattcgt   1260
gtgcttgcaa aaaataacgt gatcattcaa gatcaagaga aaaatcgagc gatttataat   1320
acagacctcc aacatgataa actagtagat cgatttgttt tttatcaaaa tagtggagaa   1380
gttaactatg ctggtagaga taatccttca agctataaag catttgcatg ggataccgat   1440
gttaccaatt atagtagtca aatgacatgg ataaatggac cagtaaatga aggccatttt   1500
ggttatattc aggcttatgc accagaatgg attcctgcaa gttgtgaacc gtttaataat   1560
atagtggatg cagaagatgt gattactcaa ataccggcag tgaaagctcg agaattaaaa   1620
tatggtgcac gtgttataaa gggtctaggt aatacaggtg gagatctagt gtctattgca   1680
cccaatggtt tgtgtgagtt gtacgtgtca tttccaaatg tagcccgaag atatcaggtc   1740
cggatacatt atgcatgtca ggatgaaacc aaaataaacc taaatatagg ggattcaagt   1800
catgatatta aacttcaatc tacgtattct ggagggcat taacatacga ttcatttggt    1860
tatgcaacaa gtgaatacag ttatctattt tatcctgatt tttatgatga aaacaaata    1920 gtacgtttag gaaatgattt tgatataaca cagcaagata tcatcattga taagattgaa   1980
tttattcctg ttgatatctt ctctgcagag gaacaggctt tagaaaaagc aagaaaggcc   2040
gtgaatgcct tgtttacagg tgatgcgaaa agtgttctaa aattgaacat cacagactat   2100
acagtggatc aagctgccaa ccttgtggaa tgtgtatcag atgaattcca tgcccaagaa   2160
aaaatgatcc tcctggatca agtgaaattc gcgaaacgat tgagtcacgc acggaatcta   2220
ctgaatcatg gtggttttga atcgccagat tggtctggag agaacggatg gaaaacaagc   2280
acacatgttt ctgtcagagc cgataaccca gtctttaaag gacgatatct ccatatgcca   2340
ggcgcgacaa attctcagtt ttctaacaat acctatccaa cgtatgtcta tcaaaaggtt   2400
gatgaatcga aattaaaatc ctatacacgg tacctggtac gcgggtttgt tggaaatagt   2460
aaagatctgg aactactagt ggagagatac ggaaaagatg tccatgtgga aatggacgta   2520
ccaaatgaca ttcggtattc tttacagacg aatgaatgtg gtggcttcga tcgctgccga   2580
```

-continued

```
cctgtatcct atcaagctcg ctcctctcat gtatgtacat gtaaggatac cgcttccatg    2640
tatacggatt atcagtgtaa agacaaagtg aatcgtactt cggccgatgt ctatacaaac    2700
gtatcgccag gtagcgcgat gtataccgat gggctccatg cccacaaatc ctgcggatgc    2760
aagaacaatg acatgtacca gagcgaaaca catcccacata agttttgcgg atgcaaagat    2820
ccacatgtct tctcgtacca tattgacaca ggatgtgtgg atcaagaaga aaaccttggt    2880
ttgtggttcg cattgaaaat tgcgagtgaa atggtgttg cgaacatcga caacctagaa    2940
atcatcgagg cacaaccact cactggggaa gcattagcac gtgtcaaaaa acgcgaacag    3000
aaatggaaac aagaaatggt aaaaaaacgc ttgcaaacag agaaagctgt acaagcagcg    3060
caaggtacga ttcagcccct attcacaaac gggcagtaca atcgtttgaa atttgaaacg    3120
ctgttctcgc aaattgtccg tgcagagtgg ctcgtccaac agattccata tgtacatcac    3180
ccattcttga gcggggcact tccagctgta ccaggcatga attttgaaat cgtccagcac    3240
ctgttggcag tgatcggaaa tgcccgtgct ttatatgaag gcggaatct tgtgcgtaat    3300 ggtacgttca gctctggtac aggaagctgg catgtgtcag aaggcgtaag ggtgaaacca    3360
ctacaaaaca cttccgtact cgttctatcg gaatggaatc atgaagcgtc ccagcagtta    3420
cgtatcgatc cagatcgcgg gtatgtgtta cgtgtaacag cccgaaaaga gggtgctgga    3480
aaaggtacgg taacgatgag tgattgtgca gattatacag agacactgac ctttacatca    3540
tgtgactata acacggttgg ttcccaagcg atgacaggtg gtacgttatc gggatttgtg    3600
acaaaaacgc tggaaatctt cccagacaca gatcgcatcc gtattgacat cggtgaaaca    3660
gaaggtacgt ttaagattga aagtgtggaa ctgatttgta tggaacagat ggagagcaac    3720
ggatag                                                                3726
```

<210> SEQ ID NO 2
<211> LENGTH: 1241
<212> TYPE: PRT
<213> ORGANISM: Bacillus thuringiensis

<400> SEQUENCE: 2

```
Met Asn Gln Asn Tyr Asn Glu Tyr Glu Ile Leu Gly Thr Gly Gly Met
1               5                   10                  15

Gly Tyr Gln Ser Arg Tyr Pro Leu Ala Lys Glu Pro Gly Ser Glu Leu
            20                  25                  30

Gln Gln Met Ser Tyr Lys Asp Trp Met Asp Arg Cys Glu Arg Gly Ser
        35                  40                  45

Leu Ala Ile Thr Phe Lys Ser Val Ile Thr Thr Ala Leu Asp Ile Thr
    50                  55                  60

Ser Ala Ile Leu Gly Ala Ala Lys Ser Pro Lys Ala Lys Val Ala Arg
65                  70                  75                  80

Ala Ala Val Gln Val Leu Asn Ala Val Ile Lys Leu Leu Trp Pro Glu
                85                  90                  95

Pro Glu Lys Pro Ser Glu Pro Ala Tyr Asp Ile Asp Phe Ile Trp Lys
            100                 105                 110

Glu Leu Ile Glu Arg Val Glu Ile Leu Ile Glu Lys Ile Asp Gln
        115                 120                 125

Glu Ala Tyr Asn Ala Ala Val Gly Arg Leu Ser Gly Leu Lys Arg Ala
    130                 135                 140

Leu Asn Leu Tyr Gln Ile Ser Phe Glu Leu Trp Val Glu Asp Glu Asn
145                 150                 155                 160
```

```
Asp Pro Glu Leu Gln Glu Asp Ile Arg Thr Arg Phe Thr Ser Ala Leu
            165                 170                 175

Phe Glu Leu Val Thr Thr Ile Glu Thr Phe Lys Tyr Asn Gly Gln Glu
        180                 185                 190

Leu Asn Leu Leu Thr Val Phe Val Gln Ala Ala Asp Phe His Leu Met
        195                 200                 205

Leu Leu Gln Gln Gly Val Met Tyr Gly Val Arg Trp Gly Phe Asp Gln
        210                 215                 220

Arg Thr Val Asp Ser Phe Tyr Gln Asn Asp Arg Gly Glu Gly Leu Lys
225                 230                 235                 240

Asp Leu Leu Thr Lys Tyr Ser Asp Tyr Ala Thr Tyr Trp Tyr Gly Glu
            245                 250                 255

Gly Leu Asn Arg Ala Lys Asn Leu Lys Ala Asn Leu Ser Asp Thr Leu
        260                 265                 270

Arg Tyr Pro Trp Ala Ala Asn Leu Glu Asp Ala Ser Val Leu Gln Glu
        275                 280                 285

Leu Glu Asp Trp Asn Leu Tyr Asn Asp Tyr Arg Arg Asp Met Thr Ile
        290                 295                 300

Leu Val Leu Asp Leu Val Ala Val Trp Pro Thr Tyr Asp Leu Arg Tyr
305                 310                 315                 320

Tyr Asp Asn Gly Asn Tyr Gly Val Gln Ser Glu Leu Thr Arg Ser Ile
            325                 330                 335

Tyr Ser Gln Ala Val Gly Asn Val Met Gly Thr Val Phe Thr Lys Glu
        340                 345                 350

Gln Tyr Glu Val Ser Phe Val Arg Pro Pro His Leu Val Thr Trp Leu
        355                 360                 365

Glu Lys Met Phe Val His Ile Arg Asp Lys Glu Gln Gly Ala Pro Ile
        370                 375                 380

Asp Ala Glu Met Ala Gly Ile Ser Leu Asp Tyr Ser Cys Ser Gly Trp
385                 390                 395                 400

Asp Asn Thr Val Tyr Asp Ile Leu Gln Gly Tyr Pro Ala Thr Gly Gly
            405                 410                 415

Ser Gln Ile Arg Val Leu Ala Lys Asn Asn Val Ile Ile Gln Asp Gln
        420                 425                 430

Glu Lys Asn Arg Ala Ile Tyr Asn Thr Asp Leu Gln His Asp Lys Leu
        435                 440                 445

Val Asp Arg Phe Val Phe Tyr Gln Asn Ser Gly Glu Val Asn Tyr Ala
        450                 455                 460

Gly Arg Asp Asn Pro Ser Ser Tyr Lys Ala Phe Ala Trp Asp Thr Asp
465                 470                 475                 480

Val Thr Asn Tyr Ser Ser Gln Met Thr Trp Ile Asn Gly Pro Val Asn
            485                 490                 495

Glu Gly His Phe Gly Tyr Ile Gln Ala Tyr Ala Pro Glu Trp Ile Pro
        500                 505                 510

Ala Ser Cys Glu Pro Phe Asn Asn Ile Val Asp Ala Glu Asp Val Ile
        515                 520                 525

Thr Gln Ile Pro Ala Val Lys Ala Arg Glu Leu Lys Tyr Gly Ala Arg
        530                 535                 540

Val Ile Lys Gly Leu Gly Asn Thr Gly Gly Asp Leu Val Ser Ile Ala
545                 550                 555                 560

Pro Asn Gly Leu Cys Glu Leu Tyr Val Ser Phe Pro Asn Val Ala Arg
            565                 570                 575

Arg Tyr Gln Val Arg Ile His Tyr Ala Cys Gln Asp Glu Thr Lys Ile
```

-continued

```
              580                 585                 590
Asn Leu Asn Ile Gly Asp Ser Ser His Asp Ile Lys Leu Gln Ser Thr
              595                 600                 605
Tyr Ser Gly Gly Ala Leu Thr Tyr Asp Ser Phe Gly Tyr Ala Thr Ser
              610                 615                 620
Glu Tyr Ser Tyr Leu Phe Tyr Pro Asp Phe Tyr Asp Glu Lys Gln Ile
625                           630                 635                 640
Val Arg Leu Gly Asn Asp Phe Asp Ile Thr Gln Gln Asp Ile Ile Ile
              645                 650                 655
Asp Lys Ile Glu Phe Ile Pro Val Asp Ile Phe Ser Ala Glu Glu Gln
              660                 665                 670
Ala Leu Glu Lys Ala Arg Lys Ala Val Asn Ala Leu Phe Thr Gly Asp
              675                 680                 685
Ala Lys Ser Val Leu Lys Leu Asn Ile Thr Asp Tyr Thr Val Asp Gln
              690                 695                 700
Ala Ala Asn Leu Val Glu Cys Val Ser Asp Glu Phe His Ala Gln Glu
705                           710                 715                 720
Lys Met Ile Leu Leu Asp Gln Val Lys Phe Ala Lys Arg Leu Ser His
                    725                 730                 735
Ala Arg Asn Leu Leu Asn His Gly Gly Phe Glu Ser Pro Asp Trp Ser
              740                 745                 750
Gly Glu Asn Gly Trp Lys Thr Ser Thr His Val Ser Val Arg Ala Asp
              755                 760                 765
Asn Pro Val Phe Lys Gly Arg Tyr Leu His Met Pro Gly Ala Thr Asn
              770                 775                 780
Ser Gln Phe Ser Asn Asn Thr Tyr Pro Thr Tyr Val Tyr Gln Lys Val
785                           790                 795                 800
Asp Glu Ser Lys Leu Lys Ser Tyr Thr Arg Tyr Leu Val Arg Gly Phe
                    805                 810                 815
Val Gly Asn Ser Lys Asp Leu Glu Leu Leu Val Glu Arg Tyr Gly Lys
              820                 825                 830
Asp Val His Val Glu Met Asp Val Pro Asn Asp Ile Arg Tyr Ser Leu
              835                 840                 845
Gln Thr Asn Glu Cys Gly Gly Phe Asp Arg Cys Arg Pro Val Ser Tyr
              850                 855                 860
Gln Ala Arg Ser Ser His Val Cys Thr Cys Lys Asp Thr Ala Ser Met
865                           870                 875                 880
Tyr Thr Asp Tyr Gln Cys Lys Asp Lys Val Asn Arg Thr Ser Ala Asp
                    885                 890                 895
Val Tyr Thr Asn Val Ser Pro Gly Ser Ala Met Tyr Thr Asp Gly Leu
              900                 905                 910
His Ala His Lys Ser Cys Gly Cys Lys Asn Asn Asp Met Tyr Gln Ser
              915                 920                 925
Glu Thr His Pro His Lys Phe Cys Gly Cys Lys Asp Pro His Val Phe
              930                 935                 940
Ser Tyr His Ile Asp Thr Gly Cys Val Asp Gln Glu Glu Asn Leu Gly
945                           950                 955                 960
Leu Trp Phe Ala Leu Lys Ile Ala Ser Glu Asn Gly Val Ala Asn Ile
                    965                 970                 975
Asp Asn Leu Glu Ile Ile Glu Ala Gln Pro Leu Thr Gly Glu Ala Leu
              980                 985                 990
Ala Arg Val Lys Lys Arg Glu Gln  Lys Trp Lys Gln Glu  Met Val Lys
              995                 1000                1005
```

| | | | | | | | | |
|---|---|---|---|---|---|---|---|---|
Lys Arg Leu Gln Thr Glu Lys Ala Val Gln Ala Ala Gln Gly Thr
       1010               1015                1020

Ile Gln Pro Leu Phe Thr Asn Gly Gln Tyr Asn Arg Leu Lys Phe
       1025               1030                1035

Glu Thr Leu Phe Ser Gln Ile Val Arg Ala Glu Trp Leu Val Gln
       1040               1045                1050

Gln Ile Pro Tyr Val His His Pro Phe Leu Ser Gly Ala Leu Pro
       1055               1060                1065

Ala Val Pro Gly Met Asn Phe Glu Ile Val Gln His Leu Leu Ala
       1070               1075                1080

Val Ile Gly Asn Ala Arg Ala Leu Tyr Glu Gly Arg Asn Leu Val
       1085               1090                1095

Arg Asn Gly Thr Phe Ser Ser Gly Thr Gly Ser Trp His Val Ser
       1100               1105                1110

Glu Gly Val Arg Val Lys Pro Leu Gln Asn Thr Ser Val Leu Val
       1115               1120                1125

Leu Ser Glu Trp Asn His Glu Ala Ser Gln Gln Leu Arg Ile Asp
       1130               1135                1140

Pro Asp Arg Gly Tyr Val Leu Arg Val Thr Ala Arg Lys Glu Gly
       1145               1150                1155

Ala Gly Lys Gly Thr Val Thr Met Ser Asp Cys Ala Asp Tyr Thr
       1160               1165                1170

Glu Thr Leu Thr Phe Thr Ser Cys Asp Tyr Asn Thr Val Gly Ser
       1175               1180                1185

Gln Ala Met Thr Gly Gly Thr Leu Ser Gly Phe Val Thr Lys Thr
       1190               1195                1200

Leu Glu Ile Phe Pro Asp Thr Asp Arg Ile Arg Ile Asp Ile Gly
       1205               1210                1215

Glu Thr Glu Gly Thr Phe Lys Ile Glu Ser Val Glu Leu Ile Cys
       1220               1225                1230

Met Glu Gln Met Glu Ser Asn Gly
       1235               1240

<210> SEQ ID NO 3
<211> LENGTH: 3723
<212> TYPE: DNA
<213> ORGANISM: Artificial Sequence
<220> FEATURE:
<223> OTHER INFORMATION: Maize optimized

<400> SEQUENCE: 3

| | |
|---|---|
| atgaatcaga actacaatga gtacgagatc cttgggaccg gaggcatggg ttatcagtca | 60 |
| cgctatccct tagcaaagga acctggcagt gagctgcaac agatgtctta caaggattgg | 120 |
| atggatcggt gcgagcgagg gtctctcgct atcactttca gtcggtgat acaactgcc | 180 |
| ctcgacatca cgtccgcaat acttggagct gcgaagagtc ccaaagcaaa ggtggcacga | 240 |
| gctgcggttc aagtactcaa tgccgtgatc aaactgctgt ggccagaacc ggagaagcct | 300 |
| tctgagccag cgtacgacat tgacttcatc tggaaggaat tgatcgagag ggtggagatt | 360 |
| ctaatcgagg aaaagatcga tcaagaggcg tacaacgctg ccgttggcag actctccggt | 420 |
| ctcaagaggg cactgaatct ctatcaaatc tccttcgagt tatgggttga agatgagaat | 480 |
| gatcctgagc tgcaagagga cattcggacg cgtttcacat ctgcactctt cgaactcgtc | 540 |
| accactatag agaccttcaa gtacaacggt caagaactca atctgctaac tgtattcgtc | 600 |

```
caagctgctg actttcatct gatgttactc cagcaaggtg ttatgtacgg tgttaggtgg      660
ggattcgatc agaggacggt cgatagcttc tatcagaacg acagagggga aggccttaag      720
gatctgctca ccaagtactc cgactacgcc acctactggt atggagaggg gttgaatagg      780
gcaaagaact tgaaggccaa cctctcagac acgctgagat atccttgggc tgcgaatctc      840
gaagatgctt ccgtcctcca agagcttgaa gattggaacc tctacaatga ctatcgtcgt      900
gacatgacaa tacttgtcct cgaccttgtc gcagtatggc ctacttacga cttgcgctac      960
tacgacaatg caactacgg tgtgcagtca gaactgacga ggtcgatcta ttcccaagcc      1020
gtgggcaatg taatggggac ggttttcaca aaagaacagt acgaagtctc ctttgttaga     1080
cctcctcacc ttgtgacttg gctggagaag atgttcgttc atacgggga taaggagcaa     1140 ggagcaccaa tcgatgccga gatggctggg atctccttag actattcttg cagtgggtgg     1200
gataacactg tgtacgacat tctgcaaggc tatccagcca cgggtggctc tcagattcgc     1260
gtgcttgcca agaacaatgt catcattcaa gatcaagaga gaatcgagc catctacaac      1320 acggacctcc agcacgacaa acttgtggac cgctttgtgt tctatcagaa cagcggagag     1380
gtgaactacg ctgggaggga caacccgtca tcatacaagg cgtttgcgtg ggacaccgat     1440
gtgacaaact actcttccca gatgacatgg atcaatggtc cggtcaacga gggacatttc     1500
ggctacatac aagcctacgc tccagaatgg attccagcga gctgcgaacc cttcaacaac     1560
atagtcgatg cggaggatgt gatcacccag attccagctg ttaaggcgag ggaactcaag     1620
tacggagcca gagtcatcaa gggcttgggc aacaccggag gcgatcttgt cagcatagca     1680
cctaatggcc tttgtgaact gtatgtctcc ttcccgaatg ttgcgaggag atatcaagta     1740
cgcatccact atgcgtgtca agatgagacc aagatcaacc taaacatcgg agatagcagc     1800
cacgacatca aactacagag tacgtactcg ggtggtgcgc taacatacga ctcctttggt     1860
tacgccacct ccgagtacag ctatctgttc tatcccgact tctacgacga gaagcagatt     1920
gtccggttgg gcaatgactt tgacatcacc cagcaagata tcatcattga caagattgag     1980
ttcattccgg ttgatatctt ctcagcagag gagcaagcct tagaaaaggc tcggaaagcg     2040
gttaacgcct tgtttactgg tgatgctaag tccgtgctca agctaaacat aacggattac     2100
actgtcgatc aagcagctaa ccttgtagaa tgtgtgagcg acgagtttca tgctcaagaa     2160
aagatgattc tccttgacca agtgaagttt gccaagcgtc tgtcccacgc tcgcaacttg     2220
ctgaatcacg gtggcttcga gtcacccgat tggtcgggag agaatggctg gaaaactagc     2280
acccatgtca gtgtgcgtgc cgacaatccc gttttcaaag ggagatatct gcacatgcct     2340
ggagctacga atagccagtt ctccaacaac acatacccga catacgtata ccagaaggtg     2400
gacgaatcga agctgaaaag ctacacacgc tatcttgtga ggggtttcgt cggcaactca     2460
aaggatctgg aattgttagt cgagcgttac ggcaaggatg tgcatgttga aatggatgtg     2520
ccgaatgata tccgctacag cttacagacg aacgagtgcg gtgggtttga ccgatgcaga     2580
cctgttagct atcaagccag atcgtcacat gtttgtactt gcaaggacac agcctccatg     2640
tacacggact atcaatgcaa ggacaaggtg aaccgcacct cagcggacgt ctacacaaac     2700
gtctctcctg gcagcgctat gtacactgat ggcttacacg cacacaagtc gtgtggctgc     2760
aagaacaatg atatgtatca gtcggaaacc caccctcata gttttgtggg gtgcaaggac     2820
cctcatgtct tttcctatca tatcgacacg ggttgtgtgg accaagagga gaatctggga     2880
ctctggtttg ctctgaagat tgcgagtgag aatggcgtcg ccaacattga caacctcgaa     2940
atcatcgaag cgcaacccct cacgggagag gcactcgctc gggttaagaa acggggagcag    3000
```

```
aaatggaaac aagagatggt gaagaagcga ctccagacgg aaaaggcagt tcaagcagcc    3060
caaggcacca tccagcctct tttcactaat ggacaataca atcgcctgaa gtttgagact    3120
ctgtttagcc agattgtcag agccgagtgg ctggtgcagc agatcccgta cgtccaccac    3180
cccttcctct ctggtgctct gccagcggtt cctggcatga acttcgagat agtccagcac    3240
cttttggctg tgatcggcaa cgcgagggca ctctacgaag gtcgaaactt ggttcggaac    3300
ggcaccttct catctggaac tggcagttgg catgtgtcag agggagtgag ggtgaagcca    3360
ctacagaaca ccagtgtgct ggtgctgagc gaatggaatc atgaggcatc gcagcagctc    3420
agaattgacc cagatcgtgg ctacgtgtta cgggtcactg caaggaagga aggagctggc    3480
aaaggcaccg tcaccatgtc ggattgcgct gattacaccg agaccttac attcacaagt     3540 tgcgactaca acacagttgg atctcaagcc atgactggtg ggacgctctc tgggttcgta    3600
acaaagacct tggaaatctt tccggacacc gacagaatcc gcatcgacat aggggagacg    3660
gaaggaacct tcaagattga gtccgtagag ttgatttgca tggagcagat ggagtctaac    3720
ggg                                                                  3723
```